United States Patent [19]

Reese

[11] 4,324,241
[45] Apr. 13, 1982

[54] HYPODERMIC SYRINGE OPERABLE WITH DOUBLE-LOOPED RING

[75] Inventor: William J. Reese, Brunswick, Ohio

[73] Assignee: Alfred D. Lobo, Cleveland, Ohio ; a part interest

[21] Appl. No.: 185,600

[22] Filed: Sep. 9, 1980

[51] Int. Cl.³ .............................................. A61M 5/00
[52] U.S. Cl. .............................................. 128/218 PA
[58] Field of Search ................................... 128/218 PA

[56] References Cited

U.S. PATENT DOCUMENTS 4,217,896  8/1980  Behnke ......................... 128/218 PA

FOREIGN PATENT DOCUMENTS 795202  5/1958  United Kingdom ......... 128/218 PA

*Primary Examiner*—John D. Yasko
*Attorney, Agent, or Firm*—Alfred D. Lobo

[57] ABSTRACT

An improved syringe assembly is provided in which a double-looped ring member comprising an index finger loop and a stem loop, permits the index finger of one hand to be inserted in the index finger loop so as to actuate withdrawal of the plunger of the syringe. Utilization of the index finger allows the exertion of a withdrawal force on the plunger along a much flatter arc than if the thumb of the same hand is used. The different articulation of the index finger of a person's hand, compared with the articulation of the thumb, allows even an elderly person to utilize the syringe assembly with one hand, without binding the plunger in the barrel of the syringe. The double-looped ring member is made of wire stock, is removably positioned on the stem of the syringe, and the stem loop is necessarily movable with respect to the stem of the plunger. Further, though the wire loops are stiff, they are manually deformable.

1 Claim, 3 Drawing Figures

HYPODERMIC SYRINGE OPERABLE WITH DOUBLE-LOOPED RING

BACKGROUND OF THE INVENTION

It is commonly required that a person use only one hand to operate a hypodermic syringe. As will readily be apparent, to operate a syringe on its forward stroke with one hand is much easier than to operate it on its rearward stroke, and it is particularly difficult to do so if the hand suffers from a lack of suppleness and dexterity due to age or arthritis. When, as so often happens, a person is both elderly and diabetic, and cannot rely on assistance to withdraw a sample of blood, it is especially important that the person be able to operate the syringe with confidence and safety.

Over the years, the problem of providing a hypodermic syringe assembly which may be used with only one hand has been attacked with numerous solutions. One of the earliest was a thumb ring attached to the end of the plunger and two finger rings attached to the syringe's barrel. In operation, the index and middle fingers were inserted in the finger rings on the barrel, and the thumb in the thumb ring. Such three-ringed syringes proved unsatisfactory, not only because they were awkward to use but because the syringe could not be properly stabilized while it was being used.

The awkwardness of the three-ring syringe was relieved by the assembly disclosed in U.S. Pat. No. 2,842,128 in which the finger rings on the barrel were dispensed with, in favor of an adjustable thumb ring which gripped the head of the plunger. Still later, in U.S. Pat. No. 3,316,909, the thumb ring was retained as an integral part of the plunger, and finger flanges were provided on the barrel to lend stability to the syringe. In both the foregoing prior art assemblies the thumb ring required the use of the thumb to withdraw the plunger and each was limited by the relatively short-radius curve of the movement of the thumb due to its physical articulation in the human hand.

SUMMARY OF THE INVENTION

It has been discovered that the peculiar articulation of the index finger of a person's hand allows safe and stable one-hand operation of the plunger of a hypodermic syringe when the plunger is withdrawn within the barrel. The index finger is inserted in an index finger loop of a double-looped ring member which is movable relative to the plunger. A stem loop of the double-looped ring member is fitted for slidable movement on the stem of the plunger, so that during operation the stem loop is lodged against the head of the plunger.

It is therefore a general object of this invention to provide a simple, convenient and reliable hypodermic syringe assembly which may be used by a person to withdraw fluid such as blood from a body using only the one hand. Exceptional stability of the syringe assembly may be had while withdrawing the plunger with the index finger, because the hand may rest against the body during the operation.

It is a specific object of this invention to provide a double-looped ring member which may be removably disposed on the stem of the plunger of a hypodermic syringe assembly only when the syringe is to be used to withdraw blood, when only one hand is available to perform the task.

It is also a specific object of this invention to provide a double-looped ring member which is formed from a continuous piece of wire stock into an index finger loop and a stem loop, the loops being stiff and generally orthogonal (that is, essentially at right angle) to one and another.

It is still another object of this invention to provide a double-looped ring member which is stiff enough to permit the withdrawal of the plunger from the barrel during operation of the syringe without substantial deformation of either loop, but flexible enough so as to be manually deformable to fit index fingers of varying size and stems of different diameter.

BRIEF DESCRIPTION OF THE DRAWINGS

The foregoing and other objects and advantages of my invention will appear more fully from the following description, made in connection with the accompanying drawings, of a preferred embodiment of the invention, wherein like reference characters refer to the same or similar parts throughout the several views, and in which.

DETAILED DESCRIPTION OF A PREFERRED EMBODIMENT

Figure 1:
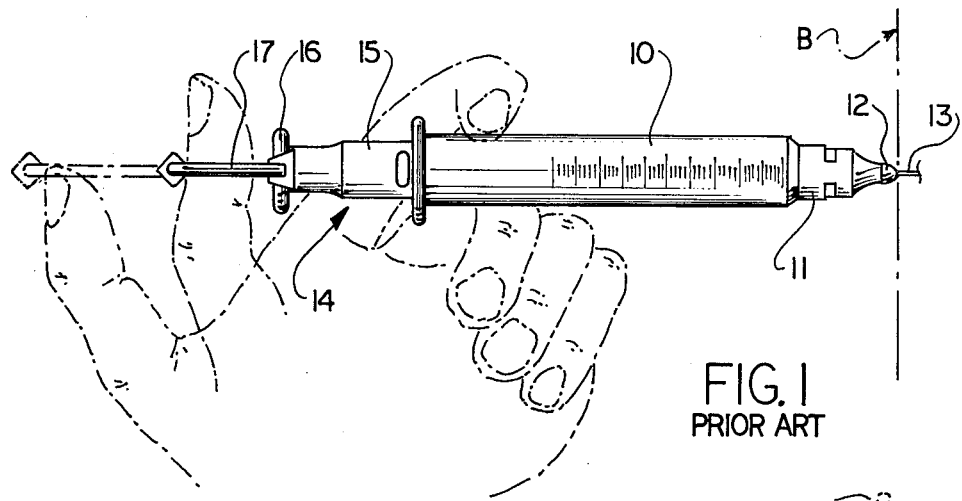
FIG. 1 is a perspective view from a slight elevation, of a prior art hypodermic syringe assembly as it is used with a thumb ring and the peculiar articulation of the thumb, as seen in its phantom position, to withdraw a sample of blood from a person's body with only one hand.

Referring to FIG. 1 of the drawing, there is shown a prior art embodiment of a hypodermic syringe assembly including a barrel 10 which is provided with a fitting 11 by means of which a hub 12 of a hypodermic needle 13 may be detachably mounted. Extending into the bore of the barrel is a plunger indicated generally by reference numeral 14, having a stem 15 terminating at one end in an actuating head 16. A rigid thumb ring 17 is fitted to the head, immovably with respect to the plunger, so that the plunger may be either thrust into the barrel for a forward stroke, or retracted from the barrel for a rearward stroke, by articulation of the thumb of the hand which holds the barrel, as shown. Typically, to give an intramuscular injection, the plunger is retracted slightly to ensure that the needle has not been inserted into a vein, and then the fluid contained in the barrel is injected by thrusting the plunger on its forward stroke, until the desired amount of fluid has been injected. If a sample of blood is to be drawn from a vein, or an intravenous injection is to be given, the needle is inserted into the body B and the plunger is retracted slightly to make sure the vein has been punctured, and then the plunger is withdrawn on its rearward stroke to draw blood into the barrel.

Particularly when an elderly person is using a hypodermic syringe to draw a sample of his own blood, it is essential that he be able to do so with confidence and safety. This means that he should be able to withdraw the plunger on its rearward stroke while holding the barrel steady, or the needle may damage a fragile vein. Referring further to FIG. 1 it will be readily apparent that it is not easy, if not virtually impossible, to hold the hand steady against the body B while holding the barrel 10 of the syringe between the index and middle fingers. As can be seen from the illustration, and much more dramatically realized in actual practice, it is difficult to have any portion of the hand resting against the body B (indicated schematically by the vertical line) while trying to operate the plunger.

Irrespective of the degree of stability one can obtain by holding the barrel of the syringe as illustrated, it will readily be apparent that the outward articulation of the thumb provides an arc of relatively short radius, less than about 5 cms, as seen in its outwardly articulated or extended position shown in phantom outline. Thus the force exerted on the thumb ring 17 to withdraw the plunger from the barrel, is exerted along an arc of relatively short radius compared to the arc generated by the articulation of the index finger, as seen in the outwardly articulated position of the index finger shown in phantom outline in FIG. 2). The effect of this thumb articulation is to exert a force along an arc (direction) which is sharply arcuate and far from longitudinally axial relative to the barrel, which tends to bind the other end of the plunger in the barrel in which the other end is supposed to be snugly but slidably fitted. Where, for example, the barrel is made of a synthetic thermoplastic material, and the plunger is also made of such material, there is sufficient flexure of the barrel and plunger so that the effect of the binding of the plunger in the barrel is negated and not detrimental. However, if the barrel is glass, as may also be the stem of the plunger, the barrel may shatter. In any event, the articulation of the thumb provides very limited and relatively sharply arcuate movement, compared to the articulation of the index finger, as will be evident in a comparison of the movements of thumb and index finger schematically illustrated in FIGS. 1 and 2.

Figure 2:
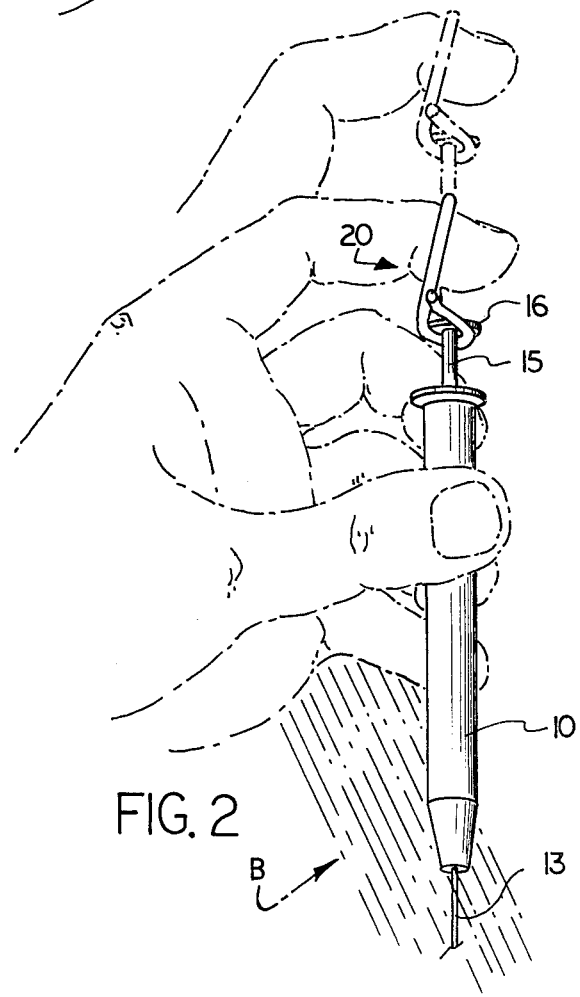
FIG. 2 is a perspective view from a slight elevation, of the hypodermic syringe assembly of the instant invention as it is used with an index finger ring of a double-looped ring member and the peculiar articulation of the index finger, as seen in its phantom position, to withdraw a sample of blood from a person's body using only one hand.

Referring further to FIG. 2 there is shown a hypodermic syringe assembly of this invention in which a double-looped ring, indicated generally by reference numeral 20, is used in combination with stem 15 of the plunger to withdraw it on its rearward stroke. The double-looped ring 20 comprises a generally circular index finger loop 21 and an elongate stem loop 22 formed from a continuous piece of wire stock so that the loops are substantially at right angle, that is orthogonal, with respect to each other. By 'wire stock' I refer to either metal or non-metal elongated stock, for example plastic, which is stiff. Index finger loop 21, as its identification implies, is formed to accomodate an index finger which should be easily insertable therein. The stem loop is formed so that it has an opening 23 in which the stem 15 maybe inserted. The stem loop 22 is thus slidable on the stem 15, and when the index finger is inserted in the index finger loop and articulated outwards, as shown in FIG. 2, the stem loop is lodged against the head 16.

The wire stock used to form the double-looped ring must be such that the loops 21 and 22 should be stiff enough to perform their function without substantial distortion. Though the double-looped ring may be very stiff, it is preferred that it be flexible enough so that the loops may be manually deformed, if desired, to conform to the index finger or to the diameter of the stem of the syringe on which the stem loop is to be slidably fitted. If the wire stock is metal, it may be sheathed in plastic, or left unsheathed. Alternatively, the double-looped ring may be injection molded as a unitary article, from nylon, polyproylene, or other stiff plastic material. It is most convenient to form the double-looped ring from plastic-coated wire stock having a diameter of about 0.075 inch.

For operation of the syringe, it will now readily be apparent that, with the index finger in the index finger loop of the double-looped ring 20, and with the barrel 10 of the syringe held between the three remaining fingers of the hand and its thumb as shown in FIG. 2, the little finger of the hand can now stabilize the hand against the body B (indicated schematically by the parallel lines). At the same time, the index finger may now be articulated outwardly so as to move the plunger on a rearward stroke along an arc of relatively large radius, greater than about 5 centimeters, thus causing substantially longitudinally axial movement of the plunger in the barrel.

Figure 3:
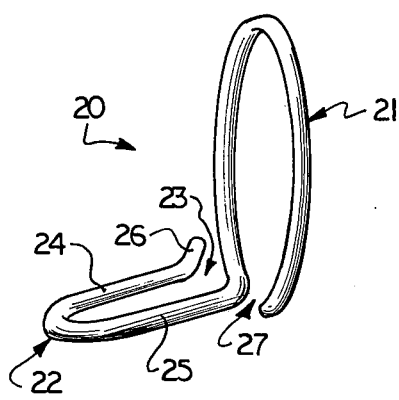
FIG. 3 is a perspective substantially side elevational view from a slight elevation, of the double-looped ring of the hypodermic syringe assembly of this invention, showing the essentially right angular disposition of the index finger loop and the stem loop relative to one and another.

Referring now to FIG. 3, there is shown a perspective substantially side elevational view of the double-looped ring 20 which shows that the index finger loop 21 is essentially at right angle to the stem loop 22. It will be noted that the stem loop is elongated, that it is provided with an opening 23 large enough to slidably accomodate the stem on which it is to be used, and that sides 24 and 25 of the stem loop are substantially parallel. The stem loop 22 is manually deformable to obtain the desired fit around the stem of any particular plunger. End 26 of the stem loop projects slightly outwards to permit easy insertion of the stem into the stem loop. A slight opening 27 is evident in the index finger loop 21 which opening may be very small or nonexistent for an index finger which is slidably insertable into the loop. The index finger loop may be manually deformed and distended to accomodate a large index finger, in which case the opening 27 will be enlarged. Thus it is seen that the double-looped ring 20 may be easily and quickly slipped on to a syringe when it is to be used, and then, after the syringe is used, just as quickly and easily removed, so that the double-looped ring can be used repetitively and indefinitely. Also, the double-looped ring is easily carried in the pocket of a garment, making it readily accessible for use.

Thus, it will now be evident that the hypodermic syringe assembly of this invention provides an unexpectedly simple and convenient solution to an old and difficult problem.

I claim:

1. A hypodermic syringe assembly to be used for withdrawing fluid into its barrel with only one hand, comprising in combination,
a plunger having a stem terminating in a head at one end, the other end being slidably snugly fitted in said barrel,
a double-looped ring member, movable with respect to said plunger and formed from a continuous piece of wire stock to provide
  (i) a generally circular index finger loop adapted to have inserted therein the index finger of the hand which holds said barrel, and (ii) a generally elongate stem loop adapted to slidably accomodate said stem and be lodged against said head, said index finger loop and said stem loop being manually deformable and generally orthogonal relative to one and another so as to permit withdrawal of said plunger with outward articulation of said index finger exerting a force along an arcuate segment having a radius of at least 5 centimeters.

* * * * *